(12) United States Patent
Chapon

(10) Patent No.: US 6,784,989 B2
(45) Date of Patent: Aug. 31, 2004

(54) PROCESS AND APPARATUS FOR REAL-TIME DETERMINATION OF A SOLID SAMPLE COMPOSITION AS A FUNCTION OF THE DEPTH WITHIN THE SAMPLE

(75) Inventor: Patrick Chapon, Villebon (FR)

(73) Assignee: Jobin Yvon S.A., Longjumeau Cedex (FR)

( * ) Notice: Subject to any disclaimer, the term of this patent is extended or adjusted under 35 U.S.C. 154(b) by 78 days.

(21) Appl. No.: 10/061,457

(22) Filed: Feb. 4, 2002

(65) Prior Publication Data

US 2002/0183940 A1 Dec. 5, 2002

(51) Int. Cl.[7] .................................................. G01J 3/30
(52) U.S. Cl. ...................... 356/311; 356/314; 356/316; 315/111.21
(58) Field of Search ................................. 356/311, 316, 356/314, 312, 313, 315, 498, 503, 451; 313/231.31; 315/111.21

(56) References Cited

U.S. PATENT DOCUMENTS

| | | | | |
|---|---|---|---|---|
| 3,809,479 A | * | 5/1974 | Whelan et al. | ............. 356/314 |
| 5,078,494 A | * | 1/1992 | Fraser | ......................... 356/311 |
| 5,081,397 A | * | 1/1992 | Liang et al. | ............ 315/111.21 |

OTHER PUBLICATIONS

Hartenstein et al, On–line Determination of Sputttered Depth in a Radio Frequency Glow Discharge Atomic Emission Source by Laser Confocal Displacement, Nov. 1999, Wiley, v. 27, pp. 962–971.*

Matthew Hartenstein et al., "On–line Determination of Sputtered Depth in a Radiofrequency Glow Discharge Atomic Emission Source By Laser Confocal Displacement", Surface and Interface Analysis, Nov. 1999, vol. 27, No. 11, pp. 962–971.

* cited by examiner

Primary Examiner—Frank G. Font
Assistant Examiner—Layla Lauchman
(74) Attorney, Agent, or Firm—Arent Fox PLLC

(57) ABSTRACT

Process and apparatus for real-time determination of a solid sample composition as a function of the depth within the sample. The process comprises: forming a glow discharge (16) of atoms sputtered from an exposed area (17) of the sample (13) and analysing the glow discharge by optical emission spectroscopy; measuring the distance between said exposed area (17) and a fixed reference surface (12a) and determining from the measured distance the depth of the exposed area within the sample; and correlating the determined depth of the exposed area with the glow discharge analysis. Application to material analysis.

13 Claims, 2 Drawing Sheets

Figure 1:
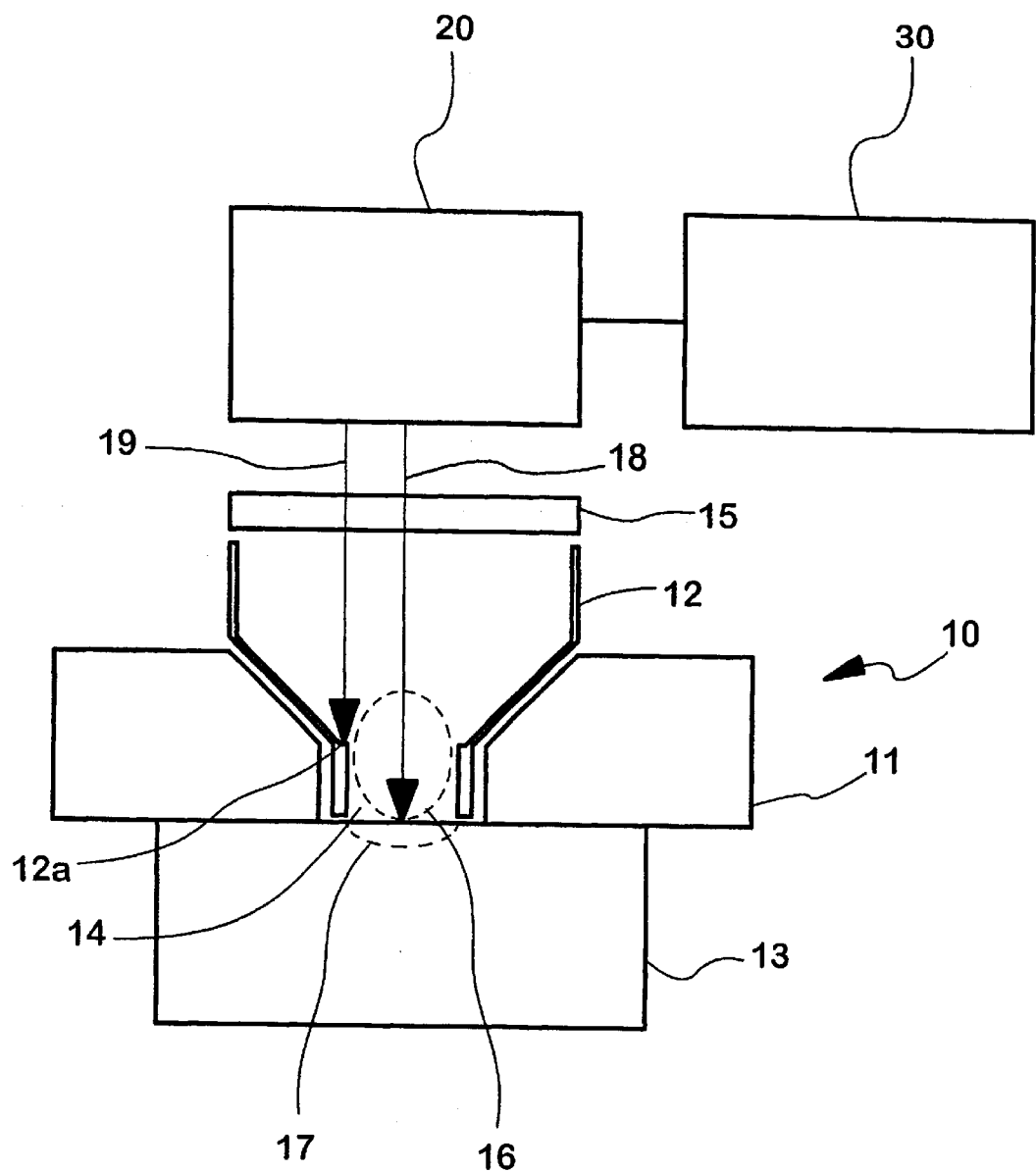

PROCESS AND APPARATUS FOR REAL-TIME DETERMINATION OF A SOLID SAMPLE COMPOSITION AS A FUNCTION OF THE DEPTH WITHIN THE SAMPLE

The present invention relates to a process and an apparatus for real-time determination of solid sample composition through glow discharge optical emission spectroscopy (GD-OES) as a function of the sputtered depth in the sample and to an apparatus for implementing the process.

As is well known, glow discharge optical emission spectroscopy (GD-OES) is a rapid technique for surface or bulk analysis of solid materials.

GD-OES combines a glow discharge with an optical emission spectrometer.

The solid sample to be analysed constitutes the cathode of the glow discharge device. The material of the cathode is impacted by positive ions of an argon plasma and sputtered atoms from the cathode enter the plasma where they are excited by collisions with the more energetic electrons or by collisions with excited metastable argon atoms. These excited atoms are de-excited by optical emission, hence producing a "glow". De-exciting atoms emit photons with characteristic wavelengths. By measuring the signals of these wavelengths, one can then measure the numbers of each type of atoms coming from the cathode and therefore the sample composition.

The crater depth formed by sputtering the sample atoms increases as the process goes on. Thus, the composition of the sample can be determined as a function of the time. These time dependant measurements can be converted in a quantitative result, i.e. a measurement as a function of the depth within the sample.

However, it necessitates a calibration and the use of calculation algorithms.

The conversion is made afterwards, i.e. after the measurement has been done.

More precisely, quantification can be carried out based on the following theoretical basis:

There are three primary processes in generation of the analytical signal:

1. the supply of sputtered atoms,
2. excitation followed by de-excitation, and
3. detection.

It is normally assumed these processes are independent.

Hence the recorded signal for a given emission line from element I is given by $$l_i = k_i \cdot e_i \cdot q_i \quad (1)$$

Where, from right to left, $q_i$ is the supply rate of element i into the plasma, $e_i$ represents the emission process, and $k_i$ is the instrumental detection efficiency.

The supply rate $q_i$, which is also the elemental sputtering rate, will vary with the concentration, $c_i$, of element i in the sample and with the overall sputtering rate, q, so that:

$$q_i = c_i \cdot q \quad (2)$$

The emission term will vary with the number of photons emitted per sputtered atom and with the absorption of these photons in traversing the plasma to reach the source window, so that:

$$e_i = S_i \cdot R_i \quad (3)$$

where $R_i$ is the emission yield and $S_i$ is a correction for self-absorption and will vary between 0 and 1 depending on the elemental sputtering rate. The detection efficiency is assumed constant. To these must be added a background term, $b_i$, originating from photomultiplier dark current, instrument noise, scattered light, argon emission and unwanted signals from nearby emission lines.

These considerations lead to the following general equation for GD-OES:

$$l_i = k_i \cdot S_i \cdot R_i \cdot c_i \cdot q + b_i \quad (4)$$

Equation (4) in fact represents a set of equations, one for each element i in the sample. If the terms $k_i$, $S_i$, $R_i$, and $b_i$ are constant then $l_i$ will vary linearly with $c_i q$.

In any analysis or at any particular depth in a depth profile, when the signals from all of the elements with significant concentrations are recorded, it can be assumed the concentrations will add up to 100%, i.e.:

$$\sum_i c_i = 1 \quad (5)$$

When the set of equations represented by equation (4) is solved simultaneously with equation (5) the solution provides note only all the concentrations at the depth where the signals were recorded but also the instantaneous sputtering rate q at that depth.

Thus, the simultaneous solution to equations (4) and (5) provides first, a set of concentrations:

$$C_i = [(l_i - b_i)/(k_i \cdot R_i \cdot S_i)]/q \quad (6)$$

and, secondly, the sputtering rate:

$$q = \sum_i (l_i - b_i)/(k_i \cdot R_i \cdot S_i) \quad (7)$$

To obtain a quantitative depth profile from equations (6) and (7), it is necessary to determine the concentration as a function of depth. To do this the value of q estimated at each depth is converted from $\mu g/s$ to $\mu m/s$, i.e. to a penetration rate w, through some assumption about density, and then these penetration rates are integrated to determine the depth, z, i.e.

$$Z = \Sigma w(t) \cdot \Delta t \quad (8)$$

This quantification is long, difficult to implement and lacks of accuracy.

It necessitates the prior measurement of the erosion rates of calibrating samples. The measurement of these erosion rates requires the use of devices such as profilemeters and balance. The error in precision of the measurement is at best of 5% which adds to other errors. Furthermore, the conversion time/depth also depends upon an estimation of the sample density in function of the chemical composition: the algorithms use for the calculation do not take perfectly into account the nature of the sample (oxides, nitrites, etc).

In summary, the measurement error is at best about 10% for known samples and can increase up to 50% for unknown samples.

Thus, the aim of the present invention is to provide a process for real-time determination of a solid sample composition through glow discharge optical emission spectroscopy which overcomes the drawbacks of the prior art processes.

The above goal is achieved according to the invention by providing a process for real-time determination of a solid sample composition which comprises:

a) forming a glow discharge of atoms sputtered from an exposed area of the sample, and analysing the glow discharge by optical emission spectroscopy;

b) measuring the distance between said exposed area and a fixed reference surface and determining from this measured distance the depth of the exposed area within the sample; and c) correlating the determined depth of the exposed area with the glow discharge analysis.

In a first implementation mode of the process of the invention, all process steps are carried out either continuously or periodically, so that there is obtained a continuous or periodical sample composition analysis as a function of the depth of the exposed area within the sample. In a second implementation mode of the process of the invention, measuring of the distance between the exposed area and the reference surface and determination of the exposed area depth is carried out at the end of the glow discharge analysing step, and the process further comprises the steps of:

d) calculating, after step (a), the theoretical depth of the exposed area within the sample using classical algorithms based on sample density estimation; and e) comparing the determined depth and the calculated depth to decide whether or not there is a clear error in the estimated sample density as indicated by a significant difference between the determined and the calculated depths.

In a third implementation mode of the process, the process is used to analyse a multilayer sample where thicknesses of the layers are approximately known and each layer contains at least a known element which can be used as an indicator of the layer.

In that case, measuring of the distance between the exposed area and the reference surface is carried out each time the indicator is highlighted in the glow discharge (either appearing or disappearing), thereby obtaining a precise determination of the positions of the layers within the sample as well as an accurate measurement of their thicknesses.

Although any kind of glow discharge device can be used in the process of the invention, radio-frequency glow discharge device is preferably used since it allows analysis of both conductive and non-conductive samples.

Measurement of the distance between the exposed area of the sample and the reference surface can be done using confocal microscopy or interferometry. Preferably, this measurement is done using laser interferometry. These measurement methods are well known per se.

The present invention also relates to an apparatus for implementing the process according to the invention which comprises:

means for creating a glow discharge of atoms sputtered from an exposed area of a sample to be analysed;

means for spectroscopically analysing the glow discharge;

means for measuring the distance between said exposed area and a reference surface;

means for determining from the measured distance, the depth of the exposed area within the sample; and means for correlating the glow discharge spectroscopic analysis with the determined depth of the exposed area.

In a preferred embodiment of the apparatus, the means for measuring the distance between the exposed area of the sample and the reference surface is a laser interferometer and the means for determining the depth of the exposed area within the sample and the correlation means are a suitably programmed computer.

Figure 2:
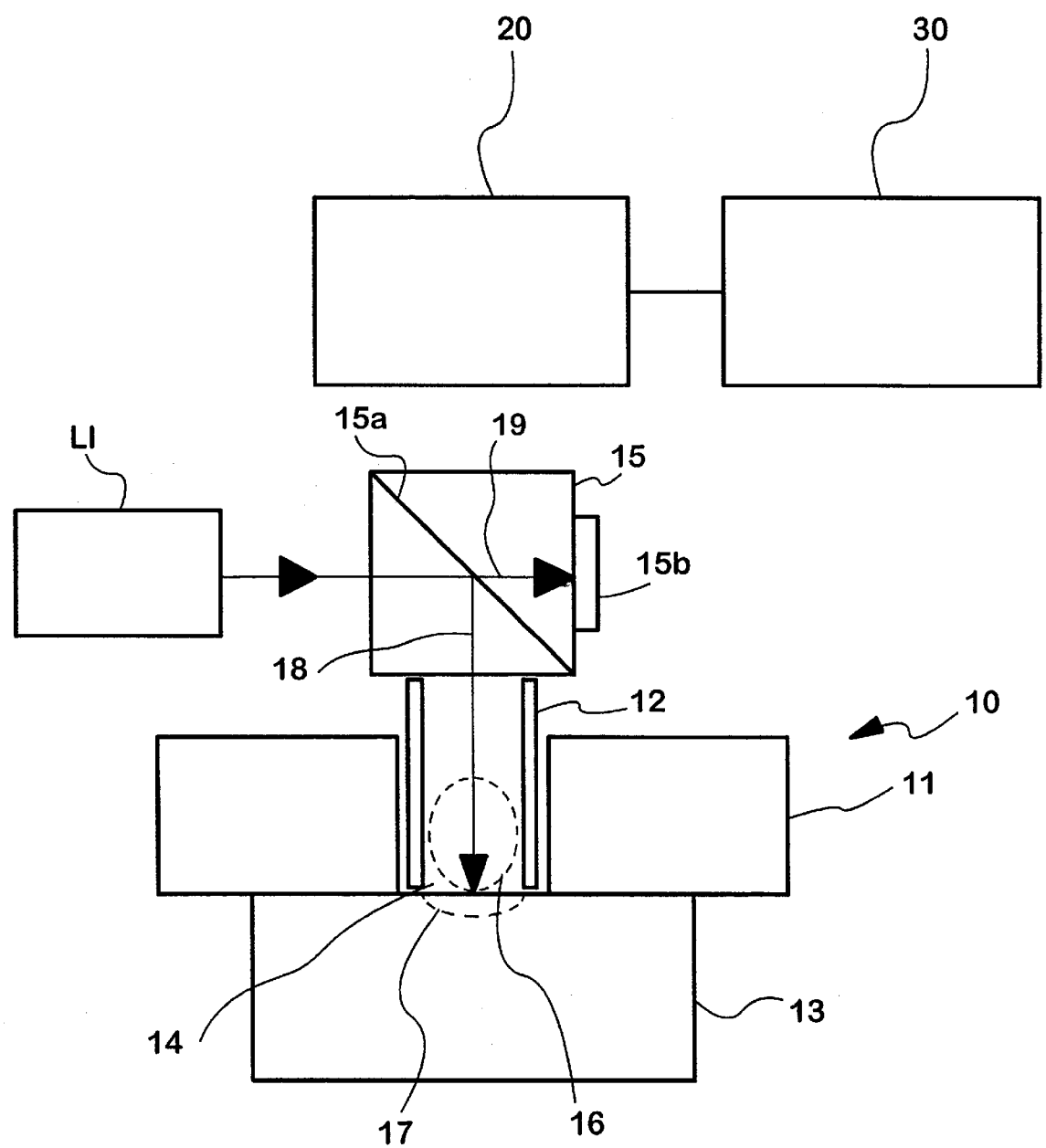

The following description is made in reference to the drawings in which:

FIG. 1 is a schematic representation of a first embodiment of an apparatus according to the invention; and FIG. 2 is a schematic representation of a second embodiment of an apparatus according to the invention.

Although the apparatus of FIGS. 1 and 2 will be now described in relation to the first implementation mode of the inventive process, they both can also be used for implementation of the two others modes.

As shown in FIG. 1, the apparatus comprises a classical RF glow discharge device 10 and an assembly 20 including an optical emission spectrometer both controlled by a computer unit 30.

Typically, the glow discharge device 10 comprises a ceramic insulating ring 11 for receiving a tubular anode 12 and holding a sample 13 to be analysed which constitutes the cathode of the device. The anode 12 defines a plasma chamber 14 just above the upper surface of the sample 13. The upper end of the tubular anode 12 is typically closed by a window 15.

According to the invention, assembly 20 further includes a laser interferometer (not shown) also controlled by the computer unit 30. When the glow discharge device 10 in energized, as is well known, a plasma 16 is formed in the plasma chamber 12. Atoms from sample 13 are sputtered by the plasma 16, and as previously explained excitation/de-excitation of the sputtered atoms create a glow discharge the intensity of which is measured by the optical emission spectrometer. Sputtering of sample atoms creates a crater 17 in the sample, the depth of which increases with time.

According to the invention, the depth of the crater 17 is measured in real-time by using the laser interferometer. The laser interferometer produces two laser beams from a single source. A first laser beam 18 is directed towards the surface of the crater 17 and a second laser beam 19 (reference beam) is directed towards a fixed reference surface 12a.

The laser beams reflected by both surfaces are then recombined to create an interferometry pattern which is used to measure the distance between the crater surface and the reference surface.

Due to the glow discharge device construction, the initial surface of the sample cannot be used as a reference surface. However, as shown in FIG. 1, a reference surface can be provided by forming a flat zone 12a on the anode. Since the sample is held against the ceramic insulating ring 11, the flat zone 12a is at a fixed reference distance from the initial surface of sample 13.

Knowing the distance separating the flat zone 12a from the surface of the crater 17, depth of the crater 17 can be determined in real-time be means of computer unit 30.

Additionally, the flat zone 12 a is formed in anode 12 outside from the plasma 16, thus assuring that the laser measurement will not affect the plasma.

As the anode may change, the initial distance between the reference surface and the sample initial surface may not be fixed in time. However, an autoscaling step may be implemented. This step is operated when the sample is pressed on the ceramic insulating ring 11 prior to any discharge and crater formation and realises a measurement of the diffraction pattern at a crater depth equal to zero. Using a typical software, such as the quantum® software, for operating the apparatus, advantage of the glow discharge flush time (typically 10 s to 60 s) can be taken to perform in masked time this measurement which will give a reference information against which the depth measurement will be calculated.

In on line measurement, the measurement is continuous and there is obtained in real-time a measurement of the glow discharge intensity as a function of the crater depth. This on-line intensity/depth measurement is then converted into a concentration/depth measurement. The algorithm used for converting intensities into concentration is the same as usual but the crater depth is directly measured, thus avoiding the main source of error in the quantification.

In FIG. 2, where the same reference numbers designate the same parts as in FIG. 1, there is shown a second embodiment of an apparatus according to the invention.

The major differences between the embodiment of FIG. 2 and the embodiment of FIG. 1, reside in the laser interferometer, the obtention of the laser beams and the positioning of the reference surface.

As shown in FIG. 2, the window 15 is cubic and includes a beam splitter 15a. A reference surface is formed on window 15 by placing a flat mirror 15b on the lateral wall of window 15 opposite to the laser source of the laser interferometer L1 and centered on the optical axis thereof. The distance between the center of mirror 15b and the sample initial surface constitutes a fixed reference distance. Autocalibration, as with the apparatus of FIG. 1, can also be implemented. Determination of the crater depth as well as correlation between sample composition and water depth is performed as with the apparatus of FIG. 1.

The apparatuses of FIGS. 1 and 2 can also be provided with lighting means and a video camera for imaging the sample area being analysed.

What is claimed is:

1. Process for real-time determination of a solid sample composition which comprises:
    (a) forming a glow discharge (16) of atoms sputtered from an exposed area (17) of the sample (13) and analysing the glow discharge by optical emission spectroscopy;
    (b) measuring the distance between said exposed area (17) and a fixed reference surface (12a) utilizing laser interferometry and determining from the measured distance the depth of the exposed area within the sample; and
    (c) correlating the determined depth of the exposed area with the glow discharge analysis.

2. Process according to claim 1, further comprising prior to step (a) an autocalibrating step of the fixed reference surface.

3. Process according to claim 2, wherein all process steps are carried out continuously or periodically.

4. Process according to claim 3, further comprising prior to step (a) an autocalibrating step of the fixed reference surface.

5. Process for teal-time determination of a solid sample composition which comprises:
    (a) forming a glow discharge (16) of atoms sputtered from an exposed area (17) of the sample (13) and analysing the glow discharge by optical emission spectroscopy;
    (b) measuring the distance between said exposed area (17) and a fixed reference surface (12a) and determining from the measured distance the depth of the exposed area within the sample; and
    (c) correlating the determined depth of the exposed area with the glow discharge analysis
    (d) calculating a theoretical depth of the exposed area (17) within the sample after step (a) using classical algorithms based on sample density estimation; and
    (e) comparing the determined depth of step (b) with the calculated theoretical depth of step (d) to decide whether or not there is a clear error in the estimated sample density as indicated by a significant difference between the determined and calculated depths.

6. Process according to claim 5, further comprising prior to step (a) an autocalibrating step of the fixed reference surface.

7. Process for real-time determination of a solid sample composition which comprises:
    (a) forming a glow discharge (16) of atoms sputtered from an exposed area (17) of the sample (13) and analysing the glow discharge by optical emission spectroscopy;
    (b) measuring the distance between said exposed area (17) and a fixed reference surface (12a) and determining from the measured distance the depth of the exposed area within the sample; and
    (c) correlating the determined depth of the exposed area with the glow discharge analysis,
    and the sample (13) is a multilayer sample, thickness of the sample layers are approximately known, each layer contains at least a known element which can be used as an indicator of the layer, and steps (b) and (c) are carried out each time an indicator is highlighted, thereby obtaining a precise determination of the positions of the layers within the sample as well as an accurate measurement of their thicknesses.

8. Process according to claim 7, further comprising prior to step (a) an autocalibrating step of the fixed reference surface.

9. Apparatus for implementing the process according to anyone of the preceding claims which comprises:
    means (10) for creating a glow discharge of atoms sputtered from an exposed area (17) of a sample (13) to be analysed;
    means (20) for spectroscopically analysing the glow discharge;
    means (18, 19, 20) for measuring the distance between said exposed area and a reference surface (12a) said means comprising a laser interferometer;
    means (30) for determining from the measured distance the depth of the exposed area (17) within the sample (13) and correlating the glow discharge spectroscopic analysis with the determined depth of the exposed area.

10. Apparatus according to claim 9, wherein said measuring means (20) comprises a means for splitting a laser beam issued from a single laser source into a first laser beam (18) directed towards the exposed area (17) of the sample and a second reference beam (19) directed towards the reference surface (12a).

11. Apparatus according to claim 10, wherein means for creating the glow discharge comprises a tubular anode (22) and the reference surface is a flat area (12a) formed in the anode.

12. Apparatus according to claim 10, wherein the means (10) for creating the glow discharge comprises a window (15) and the reference surface is formed by a mirror (15a) provided on the lateral wall of the window.

13. Apparatus according to claim 10, wherein the means for splitting the laser beam is a beam splitter (15a) arranged within the window (15).

* * * * *